United States Patent [19]

Schmid

[11] Patent Number: 5,409,824
[45] Date of Patent: Apr. 25, 1995

[54] γ-CGTASE

[75] Inventor: Gerhard Schmid, Munich, Germany

[73] Assignee: Consortium für elektrochemische Industrie GmbH, München, Germany

[21] Appl. No.: 927,316

[22] PCT Filed: Mar. 22, 1991

[86] PCT No.: PCT/EP91/00560

§ 371 Date: Sep. 23, 1992

§ 102(e) Date: Sep. 23, 1992

[87] PCT Pub. No.: WO91/14770

PCT Pub. Date: Oct. 3, 1991

[30] Foreign Application Priority Data

Mar. 27, 1990 [DE] Germany .................. 40 09 822.2

[51] Int. Cl.⁶ .................. C12N 9/10; C12N 15/54; C12P 19/18; C12R 1/07
[52] U.S. Cl. .................. 435/193; 435/101; 435/69.8; 435/I252.5; 435/832; 536/23.2
[58] Field of Search .................. 435/69.1, 69.8, 193, 435/172.3, 252.31, 320.1, 101, 252.5, 832; 536/23.2, 23.7, 24.1; 935/19, 29, 48

[56] References Cited

PUBLICATIONS

Kato, T. et al. *Agric. Biol. Chem.* 50(8):2161–2162 (1986).
Schmid, G. et al. Chem. Abstracts 112:181767e (1990). (Proc. Int. Symp. Cyclodextrins, 4th (1988), 87–92).
Kato, T. et al. Chem. Abstracts 106:29122j (1987) (*Denpun Kagaku 33(2):137–43 (1986)*).
Bender, H. *Applied Microbiol. Biotechnol.* 34:229–230 (1990).
Schmid, G. *Trends in Biotechnology* 7(9):244–248 (1989).

*Primary Examiner*—Robert A. Wax
*Assistant Examiner*—Dian C. Jacobson
*Attorney, Agent, or Firm*—Collard & Roe

[57] ABSTRACT

The invention rleates to γ-cyclodextrin glycosyl transferases obtainable by screening bacteria for the secretion of a γ-cyclodextrin glycosyl transferase, the bacteria are characterized and the γ-cyclodextrin glycosyl transferase of the bacteria is purified and characterized biochemically. These enzymes can be used for the production of γcyclodextrin from starch.

9 Claims, 10 Drawing Sheets

Fig. 2

```
            10                      30                      50
             .                       .                       .
atgattcgaaggctttcttttcacttgtggttttatttttgattagctttctagttatc
 M  I  R  R  L  S  F  S  L  V  V  L  F  L  I  S  F  L  V  I 70  AccI                90                     110
             .                       .                       .
gttaacccagagtatacagaggcaaatgaaaacttagacaatgttaattatgcccaagag
 V  N  P  E  Y  T  E  A  N  E  N  L  D  N  V  N  Y  A  Q  E 130                     150                     170
             .                       .                       .
attatttatcaaattgttacggatcgttttatgatggtgacccaactaataatcctgag
 I  I  Y  Q  I  V  T  D  R  F  Y  D  G  D  P  T  N  N  P  E 190                     210   SspI              230
             .                       .                       .
ggaactttgtttagtccaggttgtctggatttaactaaatattgtggtggggactggcaa
 G  T  L  F  S  P  G  C  L  D  L  T  K  Y  C  G  G  D  W  Q 250                     270                     290
             .                       .                       .
ggggttatcgaaaagatcgaggacgggtatttaccggatatgggcataacggctatttgg
 G  V  I  E  K  I  E  D  G  Y  L  P  D  M  G  I  T  A  I  W 310                     330                     350
             .                       .                       .
atttcgccaccaattgaaaacgttatggagcttcatccaggaggttttgcttcttatcat
 I  S  P  P  I  E  N  V  M  E  L  H  P  G  G  F  A  S  Y  H 370                     390                     410
             .                       .                       .
ggttattggggcagagatttaaacgaacaaatcctgcttttggtagtttggcagatttt
 G  Y  W  G  R  D  F  K  R  T  N  P  A  F  G  S  L  A  D  F 430                     450                     470
             .                       .                       .
tcgagattaattgaaacggctcataatcacgatataaaagtaatcatcgattttgttccc
 S  R  L  I  E  T  A  H  N  H  D  I  K  V  I  I  D  F  V  P 490                     510                     530
             .                       .                       .
aatcatacatctcctgtcgatattgagaatggagctttatatgataatggtcgtttagtt
 N  H  T  S  P  V  D  I  E  N  G  A  L  Y  D  N  G  R  L  V
```

Fig. 2 (Forts.)

```
          550                     570                    590
           .                       .                      .
gggcattattccaatgatagtgaggattattttt atacaaatggtggttcggatttctca
 G  H  Y  S  N  D  S  E  D  Y  F  Y  T  N  G  G  S  D  F  S 610                     630                    650
           .                       .                      .
agttatgaagacagtatttatcgaaatctttatgatttagctagtctaaaccagcaaaac
 S  Y  E  D  S  I  Y  R  N  L  Y  D  L  A  S  L  N  Q  Q  N 670                     690                    710
           .                       .                      .
tcatttattgatcgttatttaaaagaatcgattcaaatgtggttagatttaggaattgat
 S  F  I  D  R  Y  L  K  E  S  I  Q  M  W  L  D  L  G  I  D 730                     750                    770
           .                       .                      .
ggaattcgagtagatgcggtagcacatatgccagtagggtggcaaaagaactttgttagc
 G  I  R  V  D  A  V  A  H  M  P  V  G  W  Q  K  N  F  V  S 790                     810                    830
           .                       .                      .
tccatctatgattataatcctgtctttacatttggagaatggtttacaggtgctggtggt
 S  I  Y  D  Y  N  P  V  F  T  F  G  E  W  F  T  G  A  G  G 850                     870                    890
           .                       .                      .
agtgatgagtatcattatttattaataatagcgggatgagtgcgttagattttcgttac
 S  D  E  Y  H  Y  F  I  N  N  S  G  M  S  A  L  D  F  R  Y 910                     930                    950
           .                       .                      .
gcacaagtcgtccaagatgtgttaagaaataacgatggaacgatgtatgatttggaaaca
 A  Q  V  V  Q  D  V  L  R  N  N  D  G  T  M  Y  D  L  E  T 970                     990                    1010
           .                       .                      .
gtgttgcgagaaactgaaagcgtttacgaaaagccgcaagatcaagttacctttatcgat
 V  L  R  E  T  E  S  V  Y  E  K  P  Q  D  Q  V  T  F  I  D 1030                    1050                   1070
           .                       .                      .
aaccatgatattaatcgcttttcgagaaatggtcactcaacgcgtacaacagatttaggg
 N  H  D  I  N  R  F  S  R  N  G  H  S  T  R  T  T  D  L  G
```

Fig. 2 (Forts.)

```
        1090                1110                1130
         .                   .                   .
ttagccttttttattaacatctcgaggagtcccaaccatttattatggtactgaaatttat
 L  A  F  L  L  T  S  R  G  V  P  T  I  Y  Y  G  T  E  I  Y 1150                1170                1190
         .                   .                   .
atgacaggtgatggggacccagataatcggaaaatgatgaatacatttgatcaatcgaca
 M  T  G  D  G  D  P  D  N  R  K  M  M  N  T  F  D  Q  S  T 1210                1230                1250
         .                   .                   .
gttgcctatcaaatcatacaacagctctcttcactgcgacaagaaaatagagcgattgct
 V  A  Y  Q  I  I  Q  Q  L  S  S  L  R  Q  E  N  R  A  I  A 1270                1290                1310
         .                   .                   .
tatggggatacgacggaacgatggataaatgaagatgtatttatttatgaacgttcattt
 Y  G  D  T  T  E  R  W  I  N  E  D  V  F  I  Y  E  R  S  F 1330                1350                1370
         .                   .                   .
aatggagaatatgcacttattgctgtgaaccggagcttaaaccactcttatcagattagt
 N  G  E  Y  A  L  I  A  V  N  R  S  L  N  H  S  Y  Q  I  S 1390                1410                1430
         .                   .                   .
agcttggtaacggatatgccttctcaattatatgaagatgagctgtcaggtcttttagac
 S  L  V  T  D  M  P  S  Q  L  Y  E  D  E  L  S  G  L  L  D 1450                1470                1490
         .                   .                   .
gggcaatcgataacagtcgatcaaaatgggtctattcagccctttttgttagcaccgggt
 G  Q  S  I  T  V  D  Q  N  G  S  I  Q  P  F  L  L  A  P  G 1510                1530                1550
         .                   .                   .
gaagtaagtgtttggcaatactcaaatggtcagaatgtagcaccggaaattggtcaaatt
 E  V  S  V  W  Q  Y  S  N  G  Q  N  V  A  P  E  I  G  Q  I 1570                1590                1610
         .                   .                   .
ggtcctcctattgggaaaccaggagatgaagtgagaatcgatggttcaggctttggaagt
 G  P  P  I  G  K  P  G  D  E  V  R  I  D  G  S  G  F  G  S
```

Fig. 2 (Forts.)

```
         1630                1650                1670
          .                   .                   .
agtacgggggatgtttcttttgcgggttcaactatgaatgtattgtcttggaatgacgat
 S  T  G  D  V  S  F  A  G  S  T  M  N  V  L  S  W  N  D  D 1690                1710                1730
          .                   .                   .
acaattatagccgaactgcctgagcataatggtggaaaaaatagtgtaactgtaacgact
 T  I  I  A  E  L  P  E  H  N  G  G  K  N  S  V  T  V  T  T 1750                1770                1790
          .                   .                   .
aactcaggcgaaagcagtaatggttatccgtttgaattattaacaggtttacaaacatct
 N  S  G  E  S  S  N  G  Y  P  F  E  L  L  T  G  L  Q  T  S 1810                1830                1850
          .                   .                   .
gtcagatttgtcgtgaaccaagccgaaacgtctgttggcgaaaatctgtacgtagttggg
 V  R  F  V  V  N  Q  A  E  T  S  V  G  E  N  L  Y  V  V  G 1870                1890                1910
          .                   .                   .
gatgtacctgaattagggagctgggatcctgataaagcaattggtcctatgtttaatcaa
 D  V  P  E  L  G  S  W  D  P  D  K  A  I  G  P  M  F  N  Q 1930                1950                1970
          .                   .                   .
gttttatactcatatcccacttggtattatgatgtgagtgtacctgctaatcaagatata
 V  L  Y  S  Y  P  T  W  Y  Y  D  V  S  V  P  A  N  Q  D  I 1990                2010                2030
          .                   .                   .
gagtacaaatatattatgaaagatcaaaatggaaacgtaagctgggaaagtggaaacaac
 E  Y  K  Y  I  M  K  D  Q  N  G  N  V  S  W  E  S  G  N  N 2050                2070                2090
          .                   .                   .
catatctatagaactccagaaaattcaactggaatcgtagaagttaattttaatcaataa
 H  I  Y  R  T  P  E  N  S  T  G  I  V  E  V  N  F  N  Q  *
```

EcoRI

```
A A T T C A A T G A T T C G A A G G C T T T C T T T T C A C T T
        G T T A C T A A G C T T C C G A A A G A A A A G T G A A
            Met Ile Arg Arg Leu Ser Phe Ser Leu

G T G G T T T A T T T T T G A T T A G C T T T C T A G T T A T C G G
C A C C A A A A T A A A A A C T A A T C G A A A G A T C A A T A G C
Val Val Leu Phe Leu Ile Ser Phe Leu Val Ile
```

AccI

```
T T A A C C C A G A G T
A A T T G G G T C T C A T A
Val Asn Pro Glu
```

Oligo M10 und M11

```
         AccI
     ATACAGAGGCAGACGTAACAAACAAAGTCAATTACTCAAAAGATGTGATTTACCAGATTG
   1 ------+---------+---------+---------+---------+---------+ 60
     TGTCTCCGTCTGCTGCATTGTTGTTTCAGTTAATGAGTTTTCTACACTAAATGGTCTAAC
      T  E  A  D  V  T  N  K  V  N  Y  S  K  D  V  I  Y  Q  I  V

TTACCGATCGATTCTCTG
  61 ------+---------- 78
     AATGGC
      T
```

Oligo M12 und M13

```
                    ACGGGAATCCTGGCAACAATCCTTCAGGCGCTATCTTTAGTCAAAACT
   1 ------+---------+---------+---------+---------+---------+ 60
     TAGCTAAGAGACTGCCCTTAGGACCGTTGTTAGGAAGTCCGCGATAGAAATCAGTTTTGA
      R  F  S  D  G  N  P  G  N  N  P  S  G  A  I  F  S  Q  N  C

GTATAGAGATCTCCATAAGT
  61 ------+---------- 78
     CATATCTAGAGGTATTCA
      I  D  L  H  K
```

Fig. 7

γ-CGTASE

BACKGROUND OF THE INVENTION

1. Field of the Invention

The invention relates to cyclodextrin glycosyltransferases which primarily produce γ-cyclodextrin and which, with starch as substrate, form primarily γ-cyclodextrin and as secondary products almost exclusively cyclic oligosaccharide.

2. The Prior Art

The enzyme cyclodextrin glycosyltransferase (abbreviation: CGTase) E.C.2.4.1.19 catalyzes the formation of cyclodextrins from starch. Depending on the number of glucose units of which the cyclodextrin (CD) is composed, a distinction is made between α-CD (6 glucose units), β-CD (7 glucose units) and γ-CD (8 glucose units).

To date, two types of CGTase have been disclosed:

a) CGTases which primarily form α-cyclodextrin, also called α-CGTase, such as, for example, the CGTase from *Bacillus macerans* (U.K. Patent No. 2,169,902), from *Klebsiella pneumoniae* (EPA 220,714) and from *Bacillus stearothermophilus* (U.K. Pat. No. 2,169,902).

b) CGTases which primarily form β-cyclodextrin, or β-CGTase, such as, for example, the CGTase from *Bacillus circulans* (U.S. Pat. No. 4,477,568), from *Bacillus megaterium* (U.S. Pat. No. 3,812,011), from *Bacillus ohbensis* (Japan Patent No. 74,124,285), from Micrococcus sp. (EPA No. 017,242) and from alkalophilic Bacillus sp. (J. Gen. Microbiol. 1988, 134, 97–105; Appl. Microbiol. Biotechnol. 1987, 26, 149–153).

Concerning a γ-CGTase, to date there have been two indications in the literature:

a) The cyclodextrin glycosyltransferase from Bacillus sp. produces on addition of EtOH predominantly a mixture of β- and γ-cyclodextrin (10.4 to 18.7%) (Japan Patent No. 63,133,998). The enzyme has not been characterized in terms of its kinetic properties, so that it cannot be assigned to a specific type.

b) Two articles (Agric. Biol. Chem., 1986, 50, (8), 2161=2162 and Denpun Kagaku 1986, 33, 137) describe a γ-CGTase from *Bacillus subtilis* No. 313. This CGTase is distinguished by the formation of γ-cyclodextrin and linear oligosaccharide. Since CGTases generate only cyclic products from starch, this "CGTase" is a transitional form between an α-amylase (generates linear oligosaccharide from starch) and a CGTase. This "γ-CGTase" is unsuitable for preparing γ-cyclodextrin because only low yields can be achieved (see EPA 327,099, page 2, lines 40–43).

SUMMARY OF THE INVENTION

It is therefore an object of the present invention to prepare enzymes which predominantly produce γ-CD. The object was achieved by screening bacteria for the secretion of a γ-CGTase, characterizing these bacteria, and purifying and biochemically characterizing the γ-CGTase from the bacteria.

γ-cyclodextrin glycosyltransferases within the meaning of the invention are γ-cyclodextrin glycosyltransferases which primarily produce γ-cyclodextrin and which with starch as substrate form primarily γ-cyclodextrin and as secondary products almost exclusively cyclic oligosaccharide.

Used for screening the bacteria for the production of γ-CGTase are preferably starch-degrading, particularly preferably alkalophilic starch-degrading bacteria.

To characterize the γ-CGTase-producing bacteria, the shape, width, length and motility of the bacteria are determined. Also determined are their stainability by the Gram reaction, their ability to form catalase and their GC content. In addition, their growth behavior at various temperatures, various pH values and various NaCl concentrations are determined.

The enzyme is biochemically characterized after purification of the γ-CGTase. Thus, for example, the molecular weight, pH optimum, pH stability, temperature optimum and temperature stability of the enzyme concentrations are determined.

In order to increase the yield of γ-CGTase, the encoding gene is modified by gene manipulation and expressed in secretor mutants. For this, the gene is initially cloned and sequenced. The gene is preferably cloned in *E. coli*. The identified gene is then placed under the control of a promoter, preferably of a controllable promoter (for example $\lambda P_L$, trp, lac or trc promoter), particularly preferably of the lactose-inducible tac promoter. This makes controllable over-expression of the γ-CGTase possible. The use of a signal peptide is worthwhile for optimal secretion. The use of its own signal peptide is very suitable for γ-CGTase secretion.

A vector which, besides the γ-CGTase-encoding gene and a leader sequence, also contains regulatory elements such as, for example, the tac promoter is introduced into microorganisms, preferably *E. coli*, particularly preferably a secretor mutant of *E. coli*, for the production of the γ-CGTase. Suitable secretor mutants can be prepared by the process disclosed in EPA 338,410. The overproduction and secretion of the γ-CGTase into the culture medium can be achieved by inducing the promoter with lactose or IPTG in the case of the tac promoter. The protein according to the invention can be purified from the supernatant from the secretor mutant in a known manner.

For the first time, CGTases which primarily produce γ-cyclodextrin, and which with starch as substrate form primarily γ-cyclodextrin and as secondary products almost exclusively cyclic oligosaccharide, are prepared in the form of the enzymes described herein.

Using the genetic engineering methods described, the enzymes can be obtained in larger amounts than is possible from their natural microorganisms of origin. Using the enzyme, it is possible by the process described in U.S. Pat. No. 4,822,874 to reduce greatly the preparation times for γ-cyclodextrins.

γ-cyclodextrins increase, inter alia, the solubility of hydrophobic substances in aqueous solution, and they stabilize labile substances (for example, UV protection, oxidation protection) and bind volatile substances. γ-cyclodextrin can also be used as formulating agent. γ-cyclodextrins are used, inter alia, in the following industries: pharmaceutical, foodstuffs, cosmetics, crop protection and chemical.

The examples describe the isolation of a γ-CGTase according to the invention, the modification thereof by gene manipulation, and the overexpression of this γ-CGTase from the alkalophilic bacterium Bacillus 290-3 (DSM 5850, deposited at the DSM Deutsche Sammlung für Mikroorganismen und Zellkulturen on Mar. 19, 1990).

BRIEF DESCRIPTION OF THE DRAWINGS

Other objects and features of the present invention will become apparent from the following detailed description considered in connection with the accompanying drawings which disclose several embodiments of the present invention. It should be understood, however, that the drawings are designed for the purpose of illustration only and not as a definition of the limits of the invention.

In the drawings, wherein similar reference characters denote similar elements throughout the several views.

DETAILED DESCRIPTION OF PREFERRED EMBODIMENTS

EXAMPLE 1

Screening for γ-CGTase-producing alkalophilic bacteria

Figure 1:
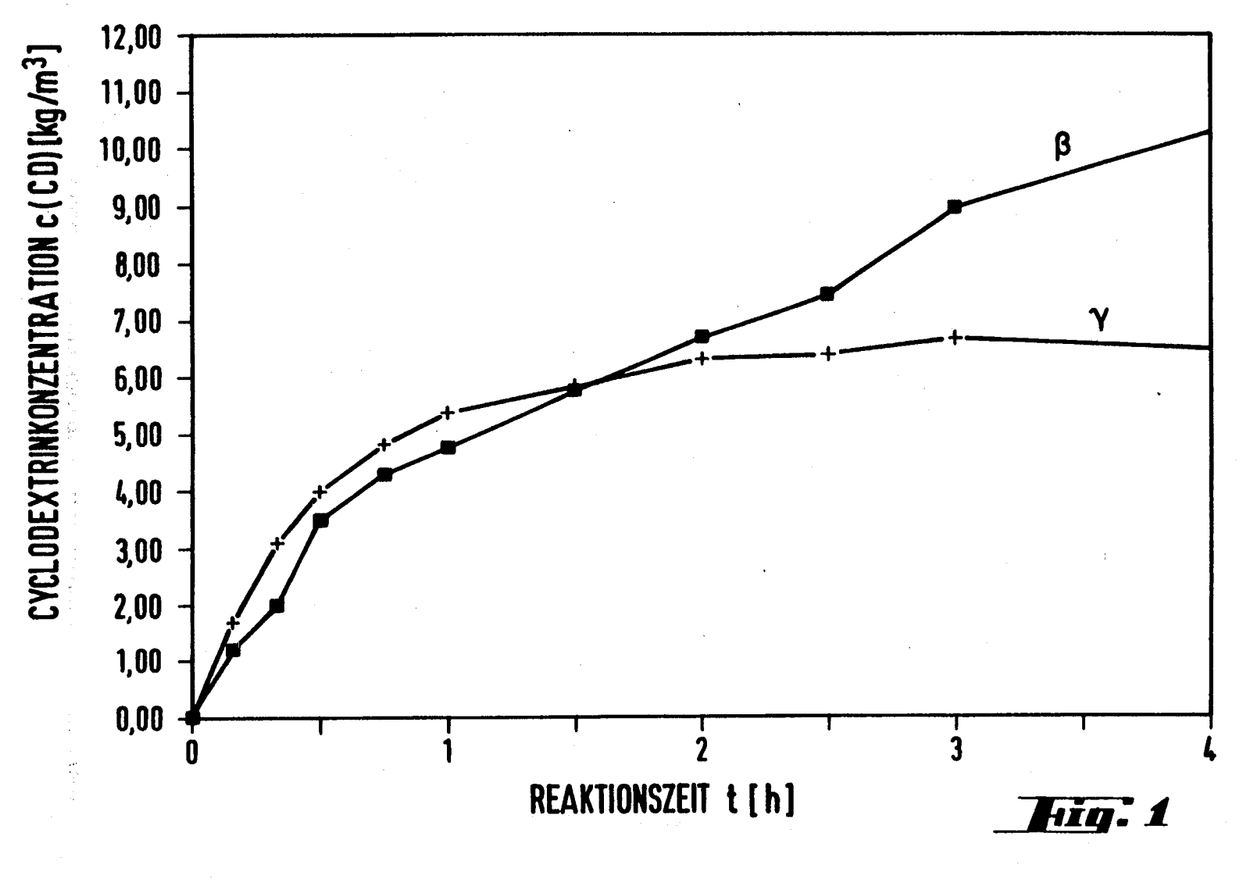
FIG. 1 shows kinetics of the production of β- and γ-cyclodextrin by the γ-CGTase from the alkalophilic bacterial strain Bacillus 290-3.

Soil samples from a very wide variety of regions of the earth were collected. 0.1–0.2 g of soil were weighed out and suspended in 1 ml of sterile physiological saline in sterile vessels. After the coarse fractions had settled out, in each case 0.1 ml was plated out on a starch agar plate (medium 1:10 g/l soluble starch, 5 g/l peptone, 5 g/l yeast extract, 1 g/l $KH_2PO_4$; 0.2 g/l $MgSO_4 \times 7 H_2O$, 10 g/l $Na_2CO_3$, 15 g/l agar, pH 10.4). The agar plates were incubated at 30° C. for two to three days. Colonies of starch-degrading bacteria showed a cloudy halo which was produced by retrogradation of low molecular weight starch molecules. The colonies were isolated and purified twice on starch agar plates. Subsequently, a culture was carried out in 2 ml of liquid medium of the above composition. After incubation at 30° C. for 48 hours, the cells were spun down and the supernatant was assayed for CGTase activity. 200 μl of supernatant were incubated with 200 μl of 10% strength starch solution in 20 mM tris/HCl pH 9.0; 5 mM $CaCl_2$ at 40° C. for one to five hours. The enzymatic reaction was stopped by adding 600 μl of methanol, and the supernatant was centrifuged and then analyzed by HPLC. The strain Bacillus 290-3 which secretes into the culture medium a CGTase which shows kinetic preference for γ-cyclodextrin formation (FIG. 1) was isolated from a large number of isolates.

EXAMPLE 2

Taxonomic characterization of the strain Bacillus 290-3

The taxonomic classification revealed that it is a Gram-positive, spore-forming bacterium which may be assigned to the Bacillus firmus/lentus complex which has not yet been accurately characterized (see Table 1).

TABLE 1

| Taxonomic features of the isolate 290-3 | |
|---|---|
| Properties | Bacillus 290-3 |
| Rods | + |
| Width μm | 0.7–0.9 |
| Length μm | 2.5–4.0 |
| Motility | + |
| Endospores | + |
| Gram reaction | + |
| Catalase | + |
| Maximum temperature | |
| Growth positive at °C. | 40 |
| Growth negative at °C. | 45 |
| Growth in | |
| Medium of pH 5.7 | − |
| Medium of pH 7.0 | − |
| NaCl 5% | + |
| 7% | + |
| mol % G + C | 36.6 |

EXAMPLE 3

Purification of the γ-CGTase

The strain Bacillus 290-3 was initially cultured in medium 1 (see Example 1). After growth for 48 hours, the cells were removed by centrifugation, and $(NH_4)_2SO_4$ was added to the culture supernatant until a saturation of 66% was reached. The mixture was stored at 4° C. for 1 hour and then the precipitate was removed by centrifugation (10,000×g; 20 min). The precipitate was resuspended in 1/100 of the initial volume in buffer A (20 mM Tris/Cl pH 8.5, 5 mM $CaCl_2$, 0.05% γ-CD) and dialyzed against the same buffer. After centrifugation (10 min., 10,000×g), the enzyme solution was loaded onto an affinity column (γ-cyclodextrin coupled to Sepharose 6B via butyl diglycidyl ether). Elution was carried out with buffer A containing 1% γ-cyclodextrin.

The eluted protein material was concentrated by ammonium sulphate precipitation and dialyzed again. The purity of the protein was checked by SDS polyacrylamide gel electrophoresis.

EXAMPLE 4

Biochemical characterization of the γ-CGTase

The biochemical characterization of the γ-CGTase gave the following results:

| | |
|---|---|
| Molecular weight | 75,000 Da |
| pH optimum | 6.0–8.0 |
| pH stability | 5.0–10.0 |
| Temp. optimum | 60° C. |
| Temp. stability | up to 50° C. |

EXAMPLE 5

Cloning and sequencing of the gene for the γ-CGTase

Cloning

Chromosomal DNA of the strain Bacillus 290-3 was partially cleaved with the restriction enzyme Sau 3A and, after size-fractionation of the fragments by agarose gel electrophoresis these DNA fragments were cloned into pUC18 (BamHI-cleaved).

$2 \times 10^4$ clones from this gene were analyzed using a radioactively labelled DNA fragment 1.6 Kb in size (BG1II-PstI) of the coding region of the γ-CGTase from Bacillus 1-1 (Proc. 4th Int. Symposium on Cyclodextrins (Huber O., Szejtli J., eds) 1988, pp. 71–76

(Kluwer Academic) in a colony-hybridization test (Maniatis et al. 1982, Cold Spring Harbor Laboratory). This resulted in identification of clones p19 and p43, whose plasmids contained the γ-CGTase gene.

Sequencing

To determine the nucleotide sequence of the γ-CGTase structural gene, DNA fragments were subcloned into the plasmid pU18 or pUC19. Exonuclease III was used to generate deletions in the inserts in these plasmids in such a way that DNA sequencing via the Sanger dideoxy chain-termination method resulted in overlapping sequences (DNA, 1985, 4, 167–170). The open reading frame which codes for the γ-CGTase comprises 2097 nucleotides, as shown in (SEQ. ID NO: 1) and FIG. 2. The protein derived therefrom consists of 699 amino acids with a molecular weight of 78,000 Da. Elimination of the signal peptide results in a molecular weight of 75,000 Da.

EXAMPLE 6

Expression and secretion of the γ-CGTase in *E. coli*

Figure 3:
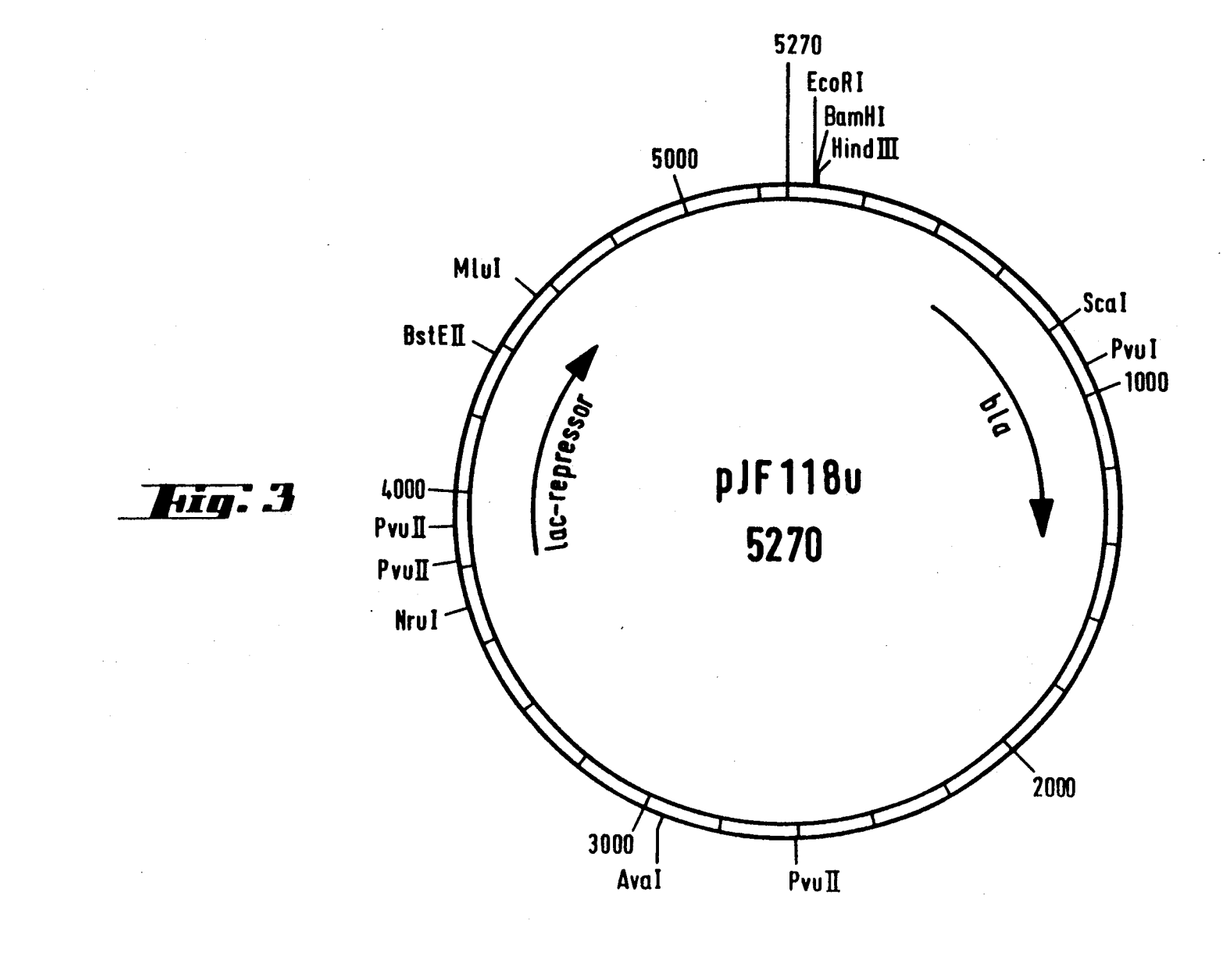
FIG. 3 shows the tac promoter plasmid pJF118u used for the overexpression of the γ-CGTase.

The tac promoter plasmid pJF118u (FIG. 3) was used for the overexpression of the γ-CGTase. The plasmid was cleaved with the restriction enzymes EcoRI and HindIII, and agarose gel electrophoresis was used to separate the small DNA fragment from the poly-linker.

Figure 4:
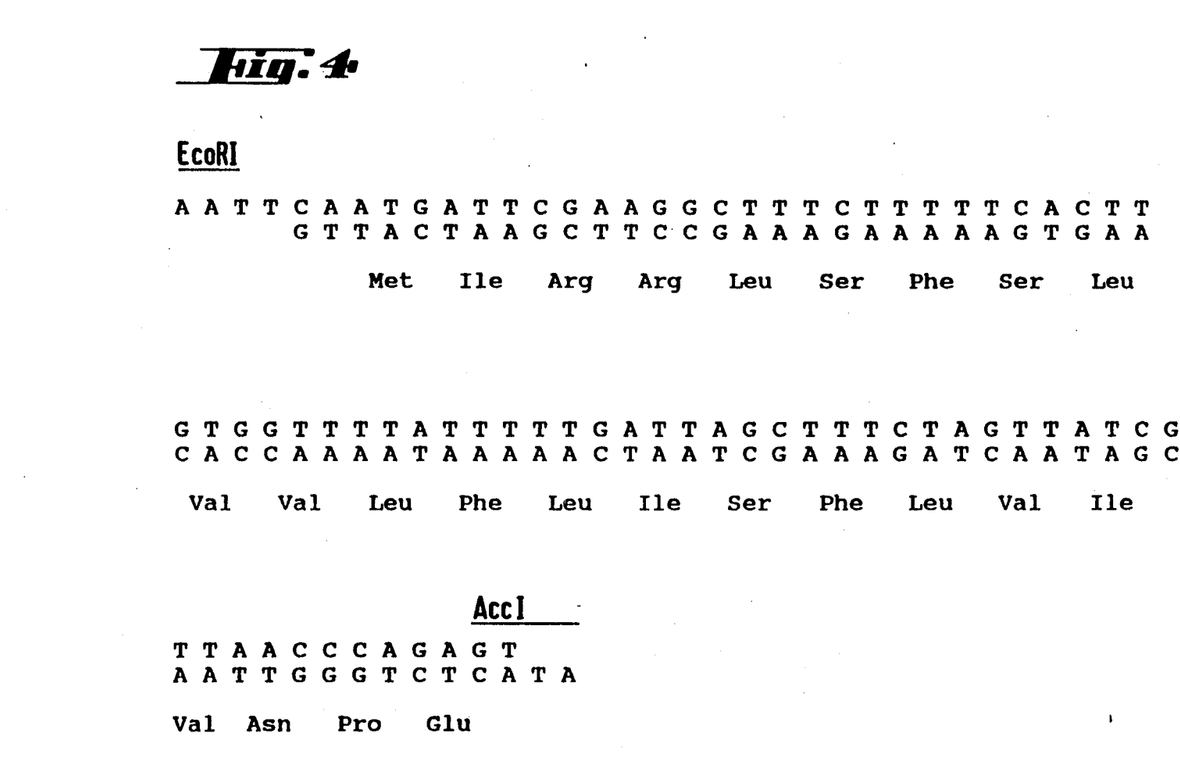
FIG. 4 shows the synthetic oligonucleotides M8 and M9.

The plasmid p19 (see Example 5) was cleaved with AccI and HindIII, and agarose gel electrophoresis was used to isolate a DNA fragment which is 2.4 kb in size and which harbors almost the complete structural gene for the γ-CGTase. Missing at the 5′ end of the gene (see "AccI site" in FIG. 2) is a short region coding for the signal peptide. Two synthetic oligonucleotides M8 and M9, as shown in (SEQ ID NO: 2) and in FIG. 4, are used to substitute for this region.

Figure 5:
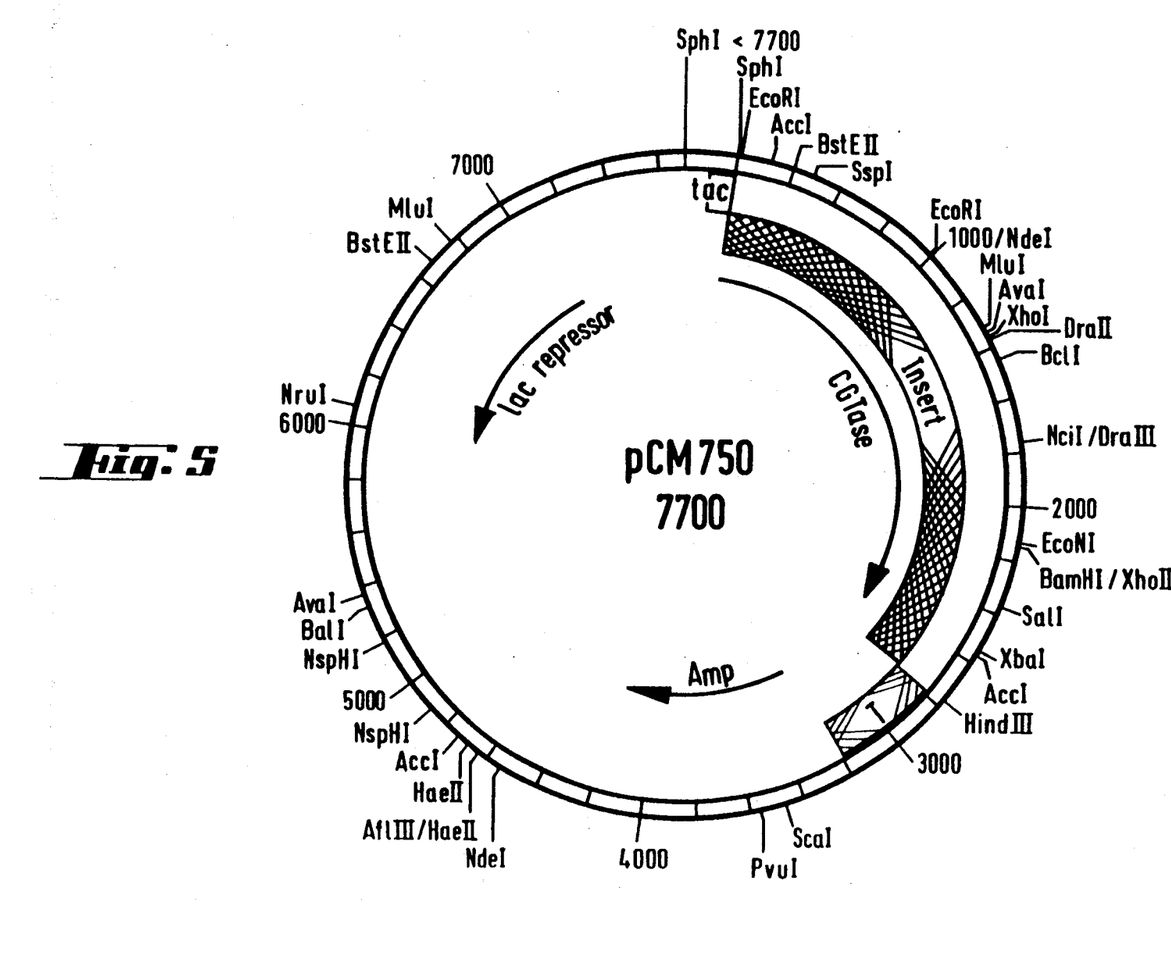
FIG. 5 shows the expression plasmid pCM750.

Ligation of the EcoRI-HindIII fragment from pJF118u with the pair of oligonucleotides M8 and M9 and the AccI-HindIII fragment of p19 resulted in the expression plasmid pCM750 (FIG. 5).

Transformation of the secretor mutant *E. coli* WCM100 with the plasmid pCM750 and initial culturing of the transformed strain in complete medium (10 g/l peptone, 5 g/l yeast extract, 5 g/l NaCl, 10 g/l lactose, 0.1 g/l CaCl₂, 100 mg/l ampicillin) at 30° C. made it possible to increase the γ-CGTase yield by a factor of 500 compared with the enzyme yields with the strain Bacillus 290-3.

EXAMPLE 7

Modification of the γ-CGTase

Figure 6:
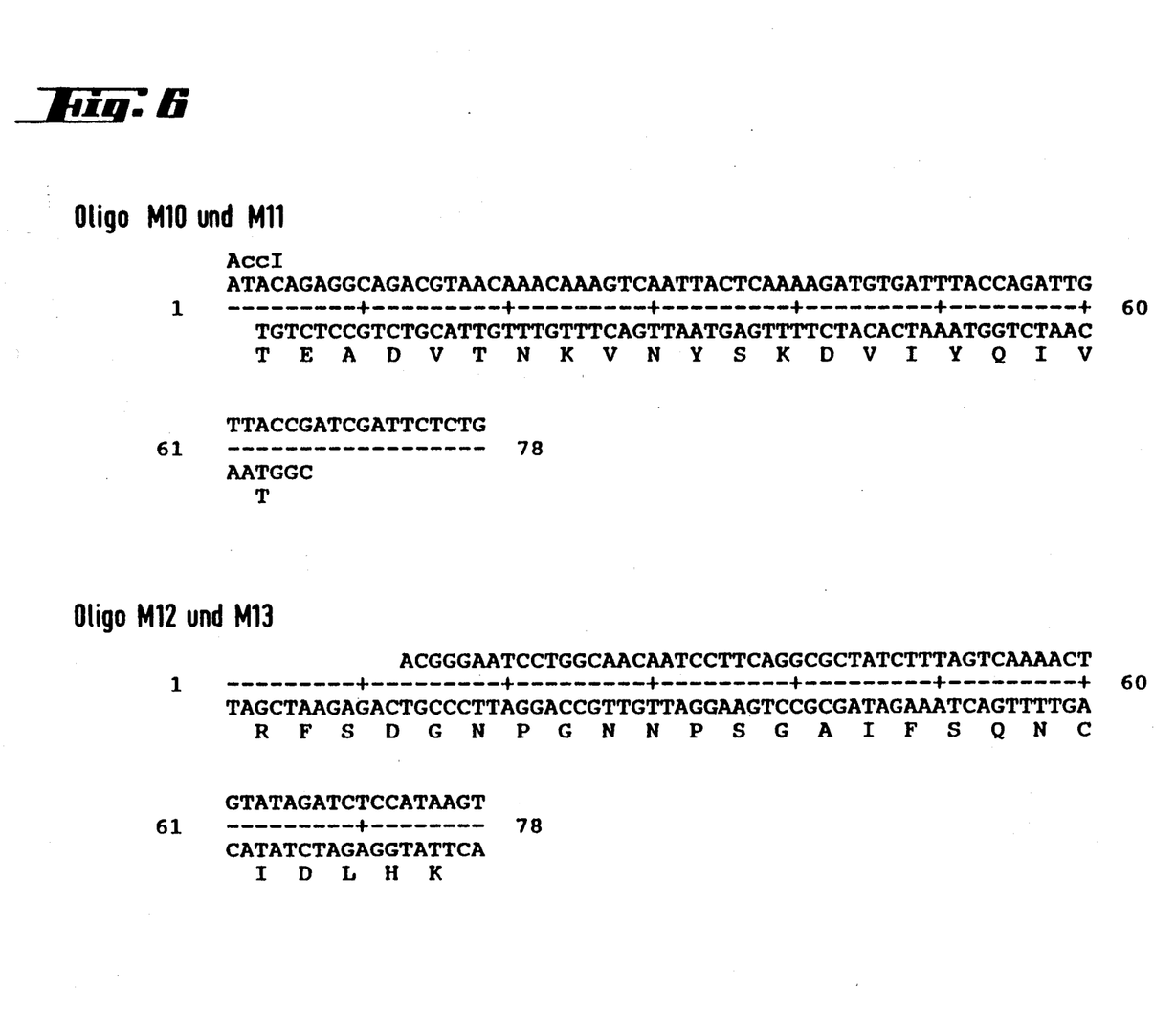
FIG. 6 shows the synthetic oligonucleotides M10, M11, M12 and M13.

The phosphoramidite method was used to synthesize the pairs of oligonucleotides M10 and M11, and M12 and M13, as shown in (SEQ ID NO: 3), in (SEQ ID NO: 4), respectively, and in FIG. 6. The DNA sequence of the oligonucleotides codes for the N-terminal amino-acid sequence of the β-CGTase from Bacillus 1-1 (Proc. 4th Int. Symposium on Cyclodextrins (Huber, O., Szejtli J., eds) 1988, pp 71–76, Kluwer Academic) and is homologous to the N-terminal region of the γ-CGTase which comprises the DNA region up to the SspI cleavage site (see FIG. 2).

Figure 7:
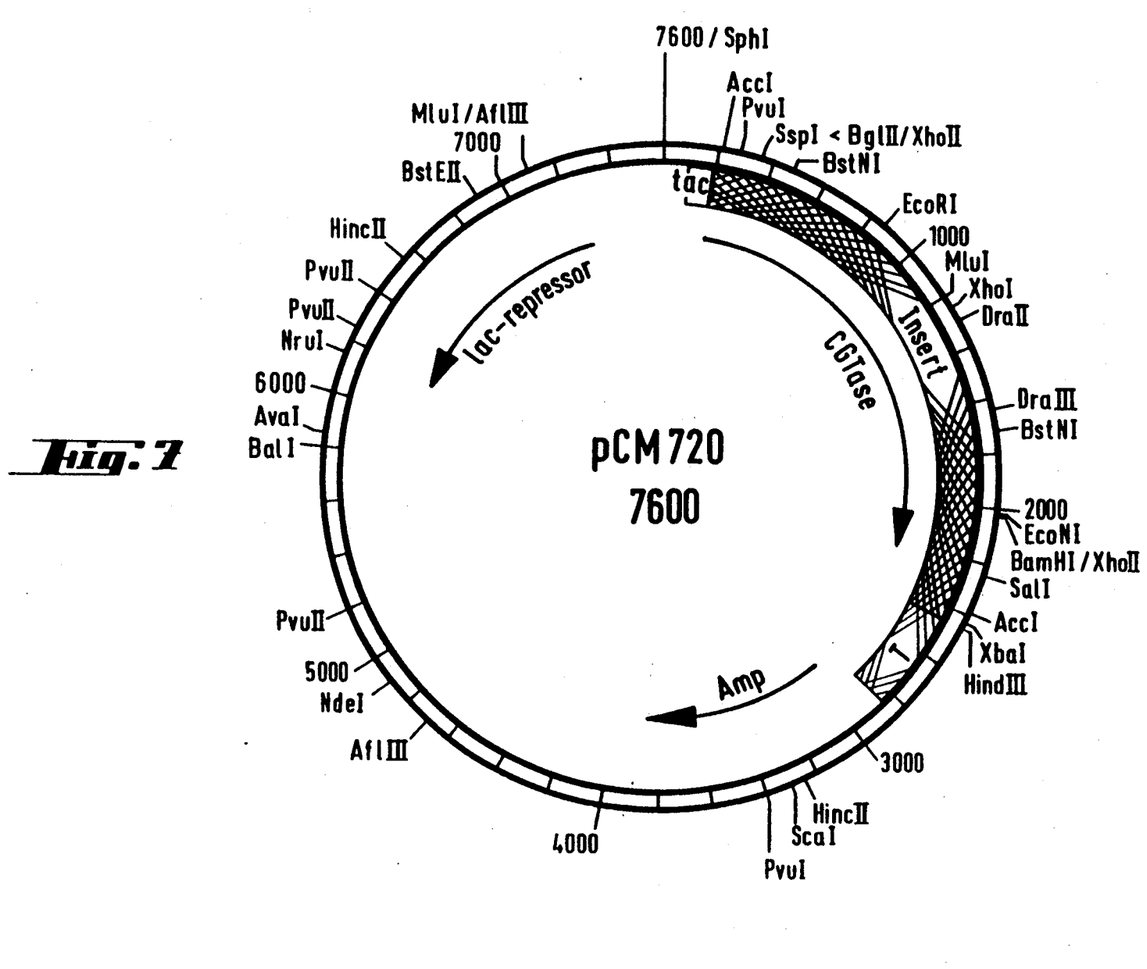
FIG. 7 shows the plasmid pCM720.

The plasmid pCM750 was partially cleaved with the restriction enzyme AccI. Subsequent cleavage was carried out with SspI, and a DNA fragment 7.3 kb in size was isolated by agarose gel electrophoresis. Ligation of this DNA fragment with the double-stranded oligonucleotides M10 and M11, and M12 and M13, resulted in the plasmid pCM720 (FIG. 7) which codes for a chimeric γ-CGTase.

Transformation of the secretor mutant *E. coli* WCM100 and initial culturing as in Example 6 resulted in doubling of the γ-CGTase yield compared with the results of Example 6.

EXAMPLE 8

Preparation of γ-cyclodextrin using the γ-CGTase 10 g of soluble starch were taken up in 100 ml of buffer (10 mmol/l tris/HCl pH 8.0 and 5 mM CaCl₂), and the starch was dissolved by heating at 95° C. for 5 min. After cooling to 50° C., 1 g of cyclohexadecenone was added as selective complexing agent for γ-cyclodextrin. Then 100 U of γ-CGTase were pipetted in. The mixture was stirred vigorously and the reaction temperature was maintained at 50° C. The optimum yield of 48% γ-cyclodextrin based on the starch used was reached after a reaction time of 8 hours.

Comparative Example

The experiment was carried out as described in Example 5 with the exception that 100 U of a γ-CGTase from *Bacillus macerans* were used in place of γ-CGTase. A maximum yield of 43% γ-cyclodextrin was reached after 32 hours.

---

I claim:

1. An isolated and purified γ-cyclodextrin glycosyltransferase from Bacillus 290-3 (DSM 5850).

Figure 2:
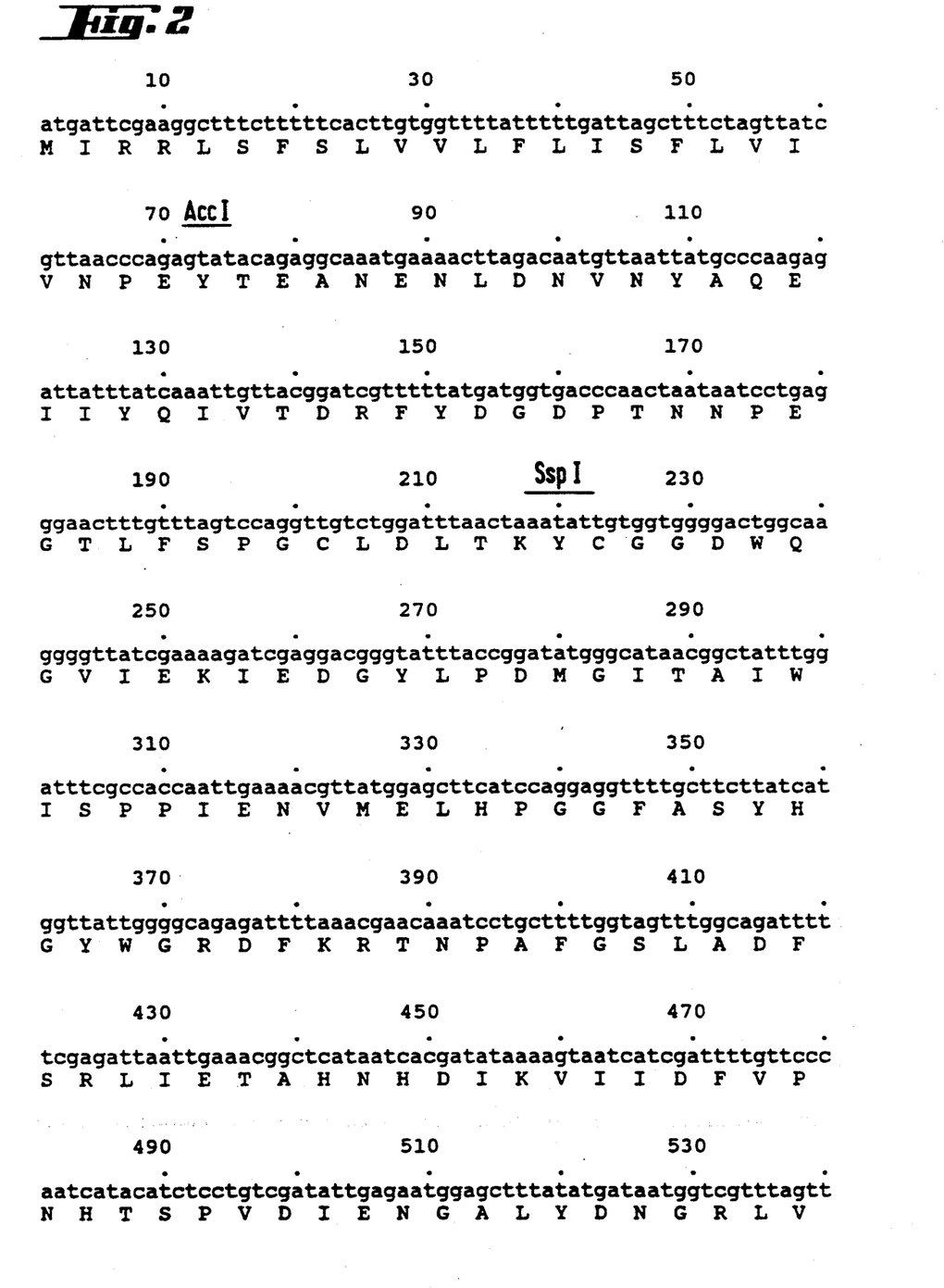
FIG. 2 shows open reading frame of the γ-CGTase from Bacillus 290-3.

2. γ-Cyclodextrin glycosyltransferase, characterized in that it is encoded by the gene of the γ-cyclodextrin glycosyl transferase according to claim 1, which is substituted from bp 75 to bp 220 by a DNA fragment encoding the amino acids of the β-CGTase from Bacillus 1-1 at the homologous positions, as shown in FIG. 2.

3. Expression plasmids which encode a cyclodextrin glycosyltransferase according to claim 1.

4. In a process for obtaining γ-cyclodextrin glycosyltransferase, the improvement comprising the steps of:
    (a) modifying a gene encoding a γ-cyclodextrin glycosyltransferase in the region encoding the 5' region of the mature protein by substituting the DNA from bp 75 to bp 220 by a DNA fragment encoding the amino acids of the β-CGTase from Bacillus 1-1 at the homologous positions, as shown in FIG. 2;
    (b) placing the modified gene under the control of a controllable promoter and introducing into a bacterium so that t is expressed with the latter; and
    (c) obtaining the enzyme from the culture supernatant after induction and expression.

5. An isolated and purified DNA encoding an amino-acid sequence as set forth in (SEQ ID NO:1).

6. An isolated and purified DNA encoding a γ-cyclodextrin glycosyltransferase, containing an amino-acid sequence starting from amino acid 75 as set forth in (SEQ ID NO: 1).

7. An isolated and purified DNA encoding a γ-cyclodextrin glycosyltransferase, containing the amino-acid regions as set forth in (SEQ ID NO:1) from amino acid 198 up to and including amino acid 214 or from amino acid 238 up to and including amino acid 247 or from amino acid 267 up to and including amino acid 275 or from amino acid 336 up to and including amino acid 343.

8. Process for the preparation of γ-cyclodextrin, characterized in that a γ-CGTase according to claim 1 is employed.

9. An isolated and purified bacterial strain Bacillus 290-3 (DSM 5850).

\* \* \* \* \*

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 2100 base pairs
        ( B ) TYPE: nucleic acid
        ( C ) STRANDEDNESS: single
        ( D ) TOPOLOGY: linear     ( i i ) MOLECULE TYPE: DNA     ( x i ) SEQUENCE DESCRIPTION: SEQ ID NO:1:

```
ATGATTCGAA  GGCTTTCTTT  TTCACTTGTG  GTTTTATTTT  TGATTAGCTT  TCTAGTTATC        60
```

```
GTTAACCCAG AGTATACAGA GGCAAATGAA AACTTAGACA ATGTTAATTA TGCCCAAGAG      120

ATTATTTATC AAATTGTTAC GGATCGTTTT TATGATGGTG ACCCAACTAA TAATCCTGAG      180

GGAACTTTGT TTAGTCCAGG TTGTCTGGAT TTAACTAAAT ATTGTGGTGG GGACTGGCAA      240

GGGGTTATCG AAAAGATCGA GGACGGGTAT TTACCGGATA TGGGCATAAC GGCTATTTGG      300

ATTTCGCCAC CAATTGAAAA CGTTATGGAG CTTCATCCAG GAGGTTTTGC TTCTTATCAT      360

GGTTATTGGG GCAGAGATTT TAAACGAACA AATCCTGCTT TTGGTAGTTT GGCAGATTTT      420

TCGAGATTAA TTGAAACGGC TCATAATCAC GATATAAAAG TAATCATCGA TTTTGTTCCC      480

AATCATACAT CTCCTGTCGA TATTGAGAAT GGAGCTTTAT ATGATAATGG TCGTTTAGTT      540

GGGCATTATT CCAATGATAG TGAGGATTAT TTTTATACAA ATGGTGGTTC GGATTTCTCA      600

AGTTATGAAG ACAGTATTTA TCGAAATCTT TATGATTTAG CTAGTCTAAA CCAGCAAAAC      660

TCATTTATTG ATCGTTATTT AAAAGAATCG ATTCAAATGT GGTTAGATTT AGGAATTGAT      720

GGAATTCGAG TAGATGCGGT AGCACATATG CCAGTAGGGT GGCAAAAGAA CTTTGTTAGC      780

TCCATCTATG ATTATAATCC TGTCTTTACA TTTGGAGAAT GGTTTACAGG TGCTGGTGGT      840

AGTGATGAGT ATCATTATTT TATTAATAAT AGCGGGATGA GTGCGTTAGA TTTTCGTTAC      900

GCACAAGTCG TCCAAGATGT GTTAAGAAAT AACGATGGAA CGATGTATGA TTTGGAAACA      960

GTGTTGCGAG AAACTGAAAG CGTTTACGAA AAGCCGCAAG ATCAAGTTAC CTTTATCGAT     1020

AACCATGATA TTAATCGCTT TTCGAGAAAT GGTCACTCAA CGCGTACAAC AGATTTAGGG     1080

TTAGCCTTTT TATTAACATC TCGAGGAGTC CCAACCATTT ATTATGGTAC TGAAATTTAT     1140

ATGACAGGTG ATGGGACCC AGATAATCGG AAAATGATGA ATACATTTGA TCAATCGACA     1200

GTTGCCTATC AAATCATACA ACAGCTCTCT TCACTGCGAC AAGAAAATAG AGCGATTGCT     1260

TATGGGGATA CGACGGAACG ATGGATAAAT GAAGATGTAT TTATTTATGA ACGTTCATTT     1320

AATGGAGAAT ATGCACTTAT TGCTGTGAAC CGGAGCTTAA ACCACTCTTA TCAGATTAGT     1380

AGCTTGGTAA CGGATATGCC TTCTCAATTA TATGAAGATG AGCTGTCAGG TCTTTTAGAC     1440

GGGCAATCGA TAACAGTCGA TCAAAATGGG TCTATTCAGC CCTTTTTGTT AGCACCGGGT     1500

GAAGTAAGTG TTTGGCAATA CTCAAATGGT CAGAATGTAG CACCGGAAAT TGGTCAAATT     1560

GGTCCTCCTA TTGGGAAACC AGGAGATGAA GTGAGAATCG ATGGTTCAGG CTTTGGAAGT     1620

AGTACGGGGG ATGTTTCTTT TGCGGGTTCA ACTATGAATG TATTGTCTTG GAATGACGAT     1680

ACAATTATAG CCGAACTGCC TGAGCATAAT GGTGGAAAAA ATAGTGTAAC TGTAACGACT     1740

AACTCAGGCG AAAGCAGTAA TGGTTATCCG TTTGAATTAT TAACAGGTTT ACAAACATCT     1800

GTCAGATTTG TCGTGAACCA AGCCGAAACG TCTGTTGGCG AAAATCTGTA CGTAGTTGGG     1860

GATGTACCTG AATTAGGGAG CTGGGATCCT GATAAAGCAA TTGGTCCTAT GTTTAATCAA     1920

GTTTTATACT CATATCCCAC TTGGTATTAT GATGTGAGTG TACCTGCTAA TCAAGATATA     1980

GAGTACAAAT ATATTATGAA AGATCAAAAT GGAAACGTAA GCTGGGAAAG TGGAAACAAC     2040

CATATCTATA GAACTCCAGA AAATTCAACT GGAATCGTAG AAGTTAATTT TAATCAATAA     2100
```

( 2 ) INFORMATION FOR SEQ ID NO:2:

( i ) SEQUENCE CHARACTERISTICS:
        ( A ) LENGTH: 79 base pairs
        ( B ) TYPE: nucleic acid
        ( C ) STRANDEDNESS: single
        ( D ) TOPOLOGY: linear     ( i i ) MOLECULE TYPE: DNA     ( x i ) SEQUENCE DESCRIPTION: SEQ ID NO:2:

```
AATTCA ATG ATT CGA AGG CTT TCT TTT TCA CTT                                    33
       Met Ile Arg Arg Leu Ser Phe Ser Leu
       1               5

GTG GTT TTA TTT TTG ATT AGC TTT CTA GTT ATC                                   66
Val Val Leu Phe Leu Ile Ser Phe Leu Val Ile
10              15                  20

GTT AAC CCA GAG T                                                             79
Val Asn Pro Gln
```

( 2 ) INFORMATION FOR SEQ ID NO:3:

( i ) SEQUENCE CHARACTERISTICS:
        ( A ) LENGTH: 78 base pairs
        ( B ) TYPE: nucleic acid
        ( C ) STRANDEDNESS: single
        ( D ) TOPOLOGY: linear     ( i i ) MOLECULE TYPE: DNA     ( x i ) SEQUENCE DESCRIPTION: SEQ ID NO:3:

```
ATACAGAGGC AGACGTAACA AACAAAGTCA ATTACTCAAA AGATGTGATT TACCAGATTG            60

TTACCGATCG ATTCTCTG                                                          78
```

( 2 ) INFORMATION FOR SEQ ID NO:4:

( i ) SEQUENCE CHARACTERISTICS:
        ( A ) LENGTH: 66 base pairs
        ( B ) TYPE: nucleic acid
        ( C ) STRANDEDNESS: single
        ( D ) TOPOLOGY: linear     ( i i ) MOLECULE TYPE: DNA     ( x i ) SEQUENCE DESCRIPTION: SEQ ID NO:4:

```
ACGGGAATCC TGGCAACAAT CCTTCAGGCG CTATCTTTAG TCAAAACTGT ATAGATCTCC            60

ATAAGT                                                                       66
```